United States Patent [19]

Grisar et al.

[11] Patent Number: 5,510,373
[45] Date of Patent: Apr. 23, 1996

[54] CARDIOPROTECTIVE AGENTS

[75] Inventors: J. Martin Grisar, Wissembourg; Margaret A. Petty, Strasbourg, both of France; Frank Bolkenius, Kehl, Germany

[73] Assignee: Merrell Pharmaceuticals Inc., Cincinnati, Ohio

[21] Appl. No.: 318,784

[22] PCT Filed: Mar. 8, 1993

[86] PCT No.: PCT/US93/02102

§ 371 Date: Oct. 5, 1994

§ 102(e) Date: Oct. 5, 1994

[87] PCT Pub. No.: WO93/20058

PCT Pub. Date: Oct. 14, 1993

[30] Foreign Application Priority Data

Apr. 6, 1992 [EP] European Pat. Off. ............. 92400957

[51] Int. Cl.⁶ .................. C07D 493/08; C07D 311/24; A61K 31/35; A61K 31/365
[52] U.S. Cl. .................. 514/455; 514/456; 549/281; 549/300; 549/400
[58] Field of Search .................. 549/281, 300, 549/400; 514/455, 456

[56] References Cited

U.S. PATENT DOCUMENTS

| | | | |
|---|---|---|---|
| 3,419,560 | 12/1968 | Bernstein et al. | 544/401 |
| 3,947,473 | 3/1976 | Scott et al. | 549/405 |
| 4,153,796 | 5/1979 | Hoehn | 546/120 |
| 4,214,081 | 7/1980 | Krapcho | 544/162 |
| 4,237,162 | 12/1980 | Kabbe et al. | 546/196 |
| 4,321,270 | 3/1982 | Sundeen | 546/196 |
| 4,617,317 | 10/1986 | Bennet | 514/458 |
| 4,694,090 | 9/1987 | Shiono et al. | 549/407 |
| 4,728,650 | 3/1988 | Eziri et al. | 514/253 |
| 4,975,457 | 12/1990 | Rupprecht et al. | 514/469 |

FOREIGN PATENT DOCUMENTS

| | | |
|---|---|---|
| 0036169 | 9/1981 | European Pat. Off. . |
| 0236120 | 9/1987 | European Pat. Off. . |
| 0281261 | 9/1988 | European Pat. Off. . |
| 0293078 | 11/1988 | European Pat. Off. . |
| 0345593 | 12/1989 | European Pat. Off. . |
| 0369083 | 5/1990 | European Pat. Off. . |
| 0369874 | 5/1990 | European Pat. Off. . |
| 0387771 | 9/1990 | European Pat. Off. . |
| 0413668 | 2/1991 | European Pat. Off. . |
| 0550337 | 7/1993 | European Pat. Off. . |
| 0536036 | 9/1993 | European Pat. Off. . |
| 2634766 | 2/1990 | France . |
| 148120 | 7/1986 | Japan . |
| 148173 | 7/1986 | Japan . |
| 215778 | 9/1990 | Japan . |
| 9320057 | 10/1993 | WIPO . |
| 9320059 | 10/1993 | WIPO . |

OTHER PUBLICATIONS

Burger, Medicinal Chemistry, 2nd Edition, Interscience Publishers, Inc., New York, (1960) pp. 72–88.

Akkerman et al., J. Chem. Soc., Perkin Trans. I, No. 9, Sep. 1979, pp. 2119–2124.

Unanue et al., Text Book of Immunology, Williams & Wilkins, Baltimore, 1984, pp. 289–294.

Koyama et al., Chemical Abstracts, vol. 111, No. 13, 115639T (1989).

*Primary Examiner*—Bernard Dentz
*Attorney, Agent, or Firm*—Carolyn D. Moon

[57] ABSTRACT

This invention relates to certain hydroxy derivatives of 3,4-dihydro-2,5,7,8-tetraalkyl-2H-1-benzopyran-2-carboxylic acids and the lactones thereof, to the processes and intermediates useful for their preparation and to their use as free radical scavengers useful in the treatment of tissue damage implicated with free oxygen radicals.

31 Claims, No Drawings

CARDIOPROTECTIVE AGENTS

This application is a 371 of PCT/U.S. Pat. No. 93/02102 filed Mar. 8, 1993.

This invention relates to certain hydroxy derivatives of 3,4-dihydro-2,5,7,8-tetraalkyl-2H-1-benzopyran-2carboxylic acids and the lactones thereof, to the processes and intermediates useful for their preparation and to their use as free radical scavengers useful in the treatment of tissue damage implicated with free oxygen radicals.

More particularly, this invention relates to compounds of the formulae

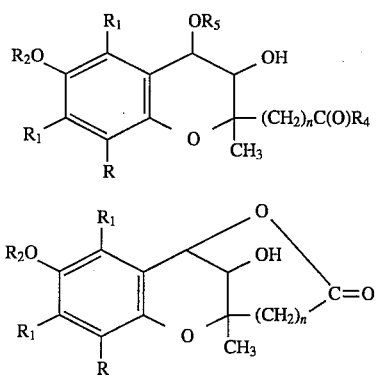

their individual isomers and mixtures thereof, and the pharmaceutically acceptable salts thereof wherein R is H or $C_{1-4}$ alkyl, $R_1$ is $C_{1-4}$ alkyl, $R_2$ is H or $C(O)R_3$, $R_3$ is H or $C_{1-9}$ alkyl, $R_4$ is OR or $N(R)_2$, $R_5$ is H, —C(O)R or $C_{1-4}$ alkyl, and n is zero or one.

As used herein the term alkyl includes the straight and branched-chain radicals having the designated number of carbon atoms with methyl and ethyl being preferred. The —C(O)$R_3$ moiety embraces formyl and the straight and branched-chain alkylcarbonyl moieties with formyl, methylcarbonyl and ethylcarbonyl being preferred. In the instance wherein $R_4$ forms an amide it is preferred that both alkyl groups be the same and that the alkyl radicals are methyl or ethyl in both mono- or di-alkylated amido situations. When variables such as R are used more than once to define a structure, it is to mean that in each instance the variable may represent a different moiety.

The compounds of the present invention include stereoisomers; the term "stereoisomer" is a general term for all isomers of individual molecules that differ only in the orientation of their atoms in space. It includes mirror image isomers (enantiomers), geometric isomers (cis/trans), and isomers of compounds with more than one chiral center that are not mirror images of one another (diastereoisomers).

In general the compounds of Formulae 1A and 1B (collectively referred to as compounds of Formula 1) may be prepared, isolated and converted to the desired salts by chemical processes, work-up and crystallization techniques analogously known in the art. Conveniently, the starting materials are either known or may be prepared by standard procedures.

The preparation of the compounds of Formula I may be schematically depicted in the following reaction schemes A and B.

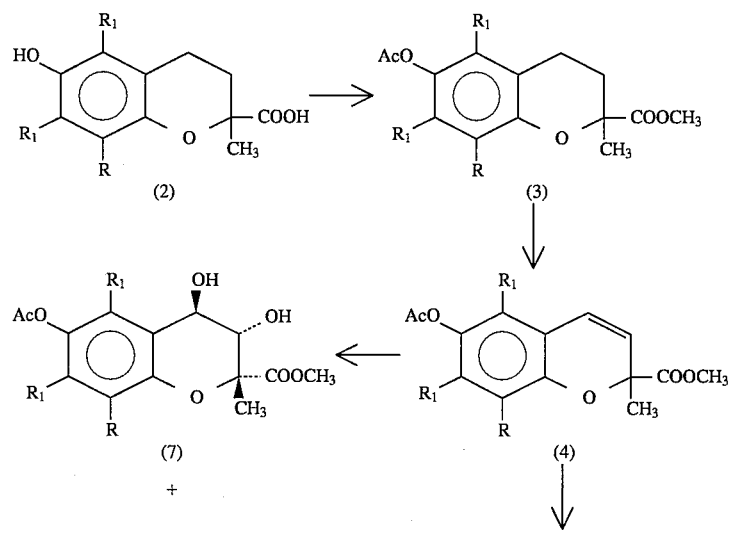

Reaction Scheme A

-continued
Reaction Scheme A

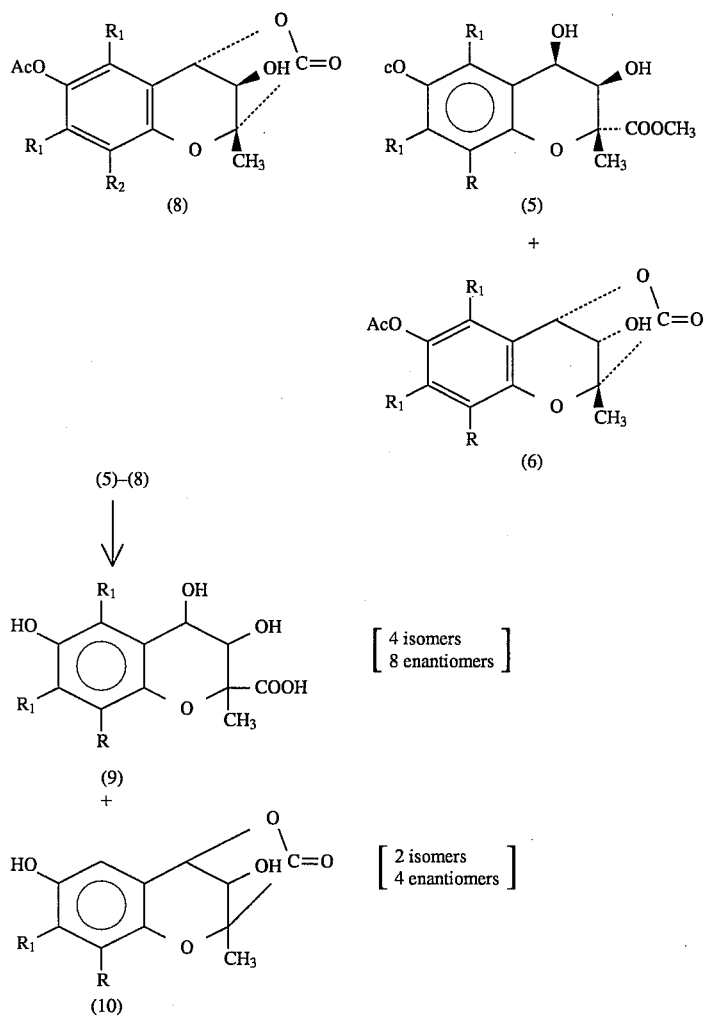

wherein R and $R_1$ are as previously defined an Ac is the preferred acyl moiety.

In this reaction sequence the acids (2) are sequentially esterified and acetylated to produce compounds (3) which are dehydrogenated, using a reagent such as DDQ (2,3-dichloro5,6-dicyano-1,4-benzoquinone) to the intermediate (4). Cis-dihydroxylation with a reagent such as osmium tetroxide gives the lactones (6) and the dihydroxyesters (5). Both can be hydrolyzed to the dihydroxy acids (9) (in which the hydroxy groups are cis- to each other) but only one can relactonize to (10). Starting with resolved (2), i.e., the R- or S-enantiomers of (2), two of the four possible enantiomers of (10), and four of the eight possible enantiomers of (9) can be obtained. Trans-dihydroxylation with a reagent such as dimethyldioxirane gives the lactones (7) and dihydroxyesters (8) which, analogously give the remaining enantiomers of (9) and (10).

Similarly, as shown in Reaction Scheme B, starting from the homologous acids (11) the foregoing process technique of Reaction Scheme A gives the δ-lactones (12) and the dihydroxy acids (13). Cis- and trans-dihydroxylation of the amides (14) gives the dihydroxy amides (15); the amides being derived by hydrolysis and amidation of compounds (4) or amidation of compounds (11).

Reaction Scheme B

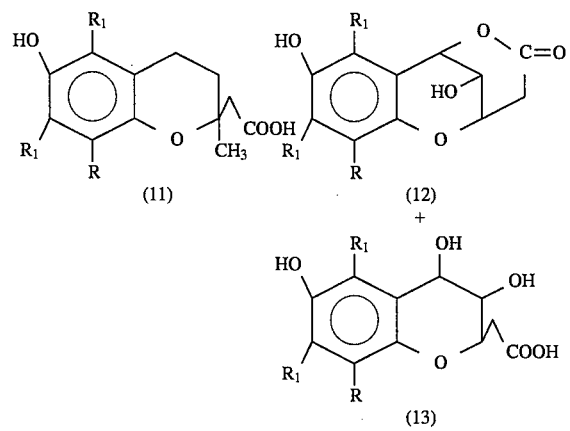

-continued
Reaction Scheme B

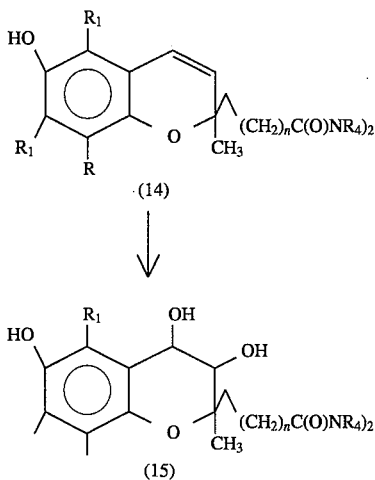

The following examples illustrate the details and techniques for the preparation of the compounds of this invention.

EXAMPLE 1

METHYL (2-R,S)-ACETYLOXY-2,5,7,8-TETRAMETHYL-2-H-1-BENZOPYRAN-2-CARBOXYLATE

A solution of 100 g of (2-R,S)-3,4-dihydro-6-hydroxy2, 5,7,8-tetramethyl-2-H-1-benzopyran-2-carboxylic acid and 1 g of p-toluene sulfonic acid in 700 ml of dry methanol is stirred at reflux temperature for 20 hours. About 400 ml of methanol is evaporated and residue is allowed to cool for crystallization. The ester is collected, washed with a little methanol, and dried.

The ester is dissolved in 500 ml of pyridine, 250 ml of acetic anhydride is added and the resulting solution is stirred overnight at room temperature. Addition of water and ice results in precipitation of the acetate that is collected, washed with water, and dried at 80° C. and 0.1 mm pressure in the presence of phosphorous pentoxide. The product can be recrystallized from a mixture of ethyl acetate and heptane.

To this ester acetate is added 1.1 equivalent (99.93 g) of 2,3-dichloro-5,6-dicyano-1,4-benzoquinone (DDQ) in 600 ml of toluene and the mixture is stirred at reflux temperature for 24–48 hours. The mixture is allowed to cool, is filtered to remove solids, and is passed through a column filled with activated alumina to remove colored material. This process may have to be repeated to remove all color. The eluate is evaporated and the residue is recrystallized from a mixture of toluene and heptane, to give 57.32 of the title compound. The NMR spectrum in $CDCl_3$ shows two doublets at δ (vs. TMS) 5.70 and 6.56 ppm with a coupling constant J=7 Hz, confirming the structure.

EXAMPLE 2

METHYL 2S-(−)-6-ACETYLOXY-2,5,7,8-TETRAMETHYL-2-H-1-BENZOPYRAN-2-CARBOXYLATE

To a hot solution of 78.07 g (311.9 mmol) of (2-R,S)-3, 4-dihydro-6-hydroxy-2,5,7,8-tetramethyl-2 H-1-benzopyran-2-carboxylic acid in 400 ml of 2-propanol is added 37.80 g (311.9 mmol) of S-(−)-α-methylbenzylamine and the solution is allowed to cool slowly in a refrigerator over several days. The resulting crystals of diastereomeric salt are collected and recrystallized 3 times from 2-propanol, again taking care slow crystallization occurs each time. The resulting product (45.13 g, 39%, m.p. 149°–50° C.) is suspended in 400 ml of water, 100 ml of 2$\underline{N}$ HCl is added, and the acid is extracted with ethyl acetate. The extract is dried over sodium sulfate, filtered, and evaporated to give 30.40 g (39%) of the S-(−)-enantiomer, m.p. 157°–9° C., $[\alpha]_D^{25}=-71.26$ (c=1.03 in $CH_3OH$).

This product is esterified, acetylated and dehydrogenated with DDQ as described in Example 1 to give the title compound, $[\alpha]_D^{25}=-246.86$ (c=1.05 in $CH_3OH$).

EXAMPLE 3

METHYL2R-(+)-6-ACETYLOXY-2,5,7,8-TETRAMETHYL-2-H-1-BENZOPYRAN-2-CARBOXYLATE

The combined filtrates from crystallization and recrystallization of the diastereomeric salt from Example 2 are evaporated and converted to free acid, 46.68 g (60%). To this residue is added 22.60 g (186.5 mmol) of R-(+)-α-methylbenzylamine in 2-propanol and, after slow crystallization and 2 recrystallizations, 48.78 g of diastereomeric salt, m.p. 149°–50° C. (mixed melting point depressed to 112°–124° C.), is obtained and converted to free acid, m.p. 157°–9° C., $[\alpha]_D^{25}=+73.75$ (c=1.04 in $CH_3OH$)

This product is esterified, acetylated, and dehydrogenated with DDQ as described in Example 1 to give the title compound, $[\alpha]_D^{25}=-217.31$ (c=1.04 in $CH_3OH$).

EXAMPLE 4

10-ANTI-(±)-7-ACETYLOXY-2,3,-DIHYDRO-10-HYDROXY-2,6,8,9 -TETRAMETHYL-2,5-METHANO-5-H-1,4-BENZODIOXEPIN-3-ONE

To 24.07 g (176.8 mmol) of N-methylmorpholine N-oxide monohydrate in 200 ml of water and 100 ml of acetone is added 5 ml of a 2.5% (w/v) solution of osmium tetroxide in t-butanol and the solution is stirred for 30 minutes. To this solution is added dropwise over 5–7 hours a solution of 51.24 g (168.4 mmol) of methyl (2-R,S)-6-acetoxy-2,5,7,8-tetramethyl-2-H-1-benzopyran-2-carboxylate, described in Example 1, in 350 ml of acetone. The mixture is stirred at room temperature overnight and at reflux temperature for 6 hours. After allowing the mixture to cool, a solution of 4 g of sodium bisulfite in 50 ml of water is added, and the mixture is stirred for 30 minutes, filtered through supercel and evaporated. During all these manipulations, care should be taken to avoid contact with the very poisonous osmium salts that should also be properly disposed of. The residue is acidified with dilute sulfuric acid and is extracted twice with ethyl acetate. The extract is washed with dilute sulfuric acid, water and a saturated sodium bicarbonate solution, dried over sodium sulfate, filtered and evaporated to give 48.57 g of an oil. Crystallization from ethyl acetate/heptane gives 38.81 g of material that was recrystallized to give 17.62 g of the title compound and 15.71 g of a second crop, described in the next example. Recrystallization of the first crop gives a pure sample of the title compound, m.p. 210°–11° C., UV ($CH_3CN$): $\lambda_{max}$ 289 (ε=1925), 282 (sh), 224 (sh), 206 (47,266); IR (KBr) 1762 $cm^{-1}$; $^1$H-NMR (DMSO); δ(ppm vs TMS) 6.49 (1, s, OH), 5.54 (1, s, 5-H), 4.43 (1, s, 10-H), 2.38 (3, s, COCH$_3$), 2.18 (3, S, Ar—CH$_3$), 2.14 (3, s, Ar—CH$_3$), 2.09 (3, s, Ar—CH$_3$), 1.69 (3, s, 2—CH$_3$).

EXAMPLE 5

METHYL TRANS, CIS-(±)-6-ACETYLOXY-3,4-DIHYDRO-3,4-DIHYDROXY-2,5,7,8-TETRAMETHYL2H-1-BENZOPYRAN-2-CARBOXYLATE

The second crop of the material obtained in the preceding example consists of two compounds, as indicated by thin layer chromatography, that can be separated by chromatography on silica gel, using mixtures of heptane and ethyl acetate, 3:1 and 2:1, for elution. One is the compound described in Example 4, the other is the title compound.

EXAMPLE 6

10-ANTI-(±)-2,3DIHYDRO-7,10DIHYDROXY-2,6,8,9-TETRAMETHYL-2,5-METHANO-5-H-1,4-BENZODIOXEPIN-3-ONE

To a solution of 17.62 g of the 7-acetate of the title compound described in Example 4, in 200 ml of methanol under nitrogen is added 100 ml of 2N NaOH. The mixture is stirred at reflux temperature for 2 hours, cooled, acidified with 2N HCl and extracted three times with ethyl acetate. The extract is washed with water and twice with a sodium bicarbonate solution, dried over sodium sulfate, filtered and evaporated. The bicarbonate washes are acidified and reextracted with ethyl acetate to give, after drying and evaporation, acidic product. This is slurried in anhydrous ethyl ether to which gaseous HCl is added. After standing at room temperature overnight, solvent and gas are evaporated, the residue is taken up in ethyl acetate and is washed with a bicarbonate solution, dried, and evaporated. The two fractions of non-acidic product thus obtained may require purification by chromatography before recrystallization from ethyl acetate/heptane to obtain the title compound, m.p. 179°–81° C. UV (CH$_3$CN)$\lambda_{max}$ 298 nm ($\epsilon$=3322), 229 (sh), 206 (39123); IR (KBr) 1766 cm$^{-1}$; $^1$H-NMR (CD$_3$OD)$\delta$ (ppm vs TMS) 5.37 (1, s, 5-H),4.23 (1, s, 10H).

EXAMPLE 7

TRANS, CIS-(±)-3,4-DIHYDRO-3,4,6-TRIHYDROXY-2,5,7,8-TETRAMETHYL-2-H1-BENZOPYRAN-2-CARBOXYLIC ACID

The 6-acetate methyl ester of the title compound, described in Example 5, is stirred with 1N 50% methanolic NaOH under nitrogen for 5 hours at reflux temperature. After cooling, the solution is acidified with 2N HCl and extracted with ethyl acetate. The extract is washed with water and twice with a sodium bicarbonate solution. The bicarbonate washes are acidified, saturated with sodium chloride and extracted 4 times with ethyl acetate. After drying over sodium sulfate, filtration and evaporation of solvent, an oil is obtained that crystallizes from ethyl acetate/heptane to give the title compound. UV (CH$_3$CN)$\epsilon_{max}$ 295 nm ($\epsilon$=3802), 223 (sh), 201 (35620); IR (KBr) 1717 cm$^{-1}$; $^1$H-NMR (D$_2$O)$\delta$ (ppm vs TMS) 4.78 (1, s, 4-H), 4.32 (1, s, 3-H), 2.19–2.22 (9, 3s, Ar—CH$_3$), 1.70 (3, s, 2—CH$_3$).

EXAMPLE 8

10-ANTI-(+)-(2S, 5R, 10R)-7-ACETYLOXY-2,3,-DIHYDRO-10HYDROXY-2,6,8,9-TETRAMETHYL-2,5-METHANO-5-H-1,4-BENZODIOXEPIN-3-ONE

Starting with 12.18 g of the 2S-enantiomer described in Example 2 and utilizing the procedure described in Example 4, 11.98 g of crude product is obtained. Crystallization from 40 ml of ethyl acetate gives 2.49 g of product. Chromatography of the filtrate on silica gel (elution with ethyl acetate/heptane: ½) gives a fraction containing an additional 3.7 g of the same product and recrystallization of the combined product from ethyl acetate/heptane gives 5.01 g (41%) of the title compound, m.p. 201°–5° C., [α]$_D^{25}$=+58.92 (c=1.02 in CH$_3$OH). UV, IR, and $^1$H-NMR correspond to those of the racemic compounds described in Example 4.

EXAMPLE 9

10-ANTI-(+)-(2S, 5R, 10R)-2,3-DIHYDRO-7,10-DIHYDROXY 2,6,8,9TETRAMETHYL-2,5-METHANO-5-H-1,4BENZODIOXEPIN-3ONE

The 7-acetate of the title compound, described in the preceding example is hydrolyzed and relactonized by the procedure described in Example 6 to give the title compound, m.p. 172°–3° C., [α]$_D^{25}$=+63.24 (c=1.05 in CH$_3$OH). UV, IR, and $^1$H-NMR correspond to those of the racemic compound, described in Example 6.

EXAMPLE 10

10-ANTI-(−)-(2R, 5S, 10S)-7-ACETYLOXY-2,3,-DIHYDRO-10-HYDROXY-2,6,8,9-TETRAMETHYL-2,5-METHANO-5-H-1,4-BENZODIOXEPIN-3-ONE

The antipode of the compound described in Example 8 is obtained in 50% yield by the same procedure but starting from the R-enantiomer described in Example 3. m.p. 210°–1° C., [α]$_D^{25}$=−63.32 (c=1.15 in CH$_3$OH). UV, IR, and $^1$H-NMR spectra correspond to those of the (+)-enantiomer and the racemate, described in Example 4.

EXAMPLE 11

CIS, CIS-(+)(2R, 3S, 4S)-3,4-DIHYDRO-3,4,6-TRIHYDROXY-2,5,7,8TETRAMETHYL-2-H-1BENZOPYRAN-2-CARBOXYLIC ACID

To 3.06 g (1 mmol) of the lactone acetate described in the preceding example, in 50 ml of methanol under nitrogen is added 50 ml of 2N sodium hydroxide and the mixture is heated to reflux temperature for 20 minutes The resulting solution is cooled, acidified with 60 ml of 2N hydrochloric acid, and concentrated to remove methanol. The remaining aqueous solution is extracted four times with ethyl ether and extract washed with a sodium bicarbonate solution. The aqueous phase is combined with the bicarbonate washes, carefully acidified with a minimum of 2N hydrochloric acid, saturated with sodium chloride, and extracted four times with ethyl acetate. The extract is dried over sodium sulfate, filtered and evaporated to give 2.87 g of the title compound, m.p. 115° C. (dec.),[α]$_D^{25}$=+57.45°(c=1.02 in MeOH). UV (CH$_3$CN)$\epsilon_{max}$ 295 nm ($\lambda$=3530), 225 (sh), 204 (35820); IR (KBr) 1718 cm$^{-1}$; $^1$H-NMR (DMSO) δ (ppm vs TMS) 4.67

(1, d, J =3.8, 4-H), 3.82 (1, d, J =3.8, 3-H), 2.1–2.2 (9, 3s, Ar—CH$_3$), 1.62 (3, s, 2—CH$_3$); Anal.: C, H. The NMR spectrum indicates that the compound contains about 10% of the lactone described in the next example.

EXAMPLE 12

10-ANTI-(−)-(2R,5S,10S)-2,3-DIHYDRO-7,10-DIHYDROXY-2,6,8,9-TETRAMETHYL-2,5-METHANO-5-H1,4-BENZODIOXEPIN-3-ONE

The crystallization mother liquor, obtained in the preceding example, is evaporated, suspended in anhydrous ethyl ether, and gaseous hydrogen chloride is bubbled in. The mixture is allowed to stand at room temperature overnight and is evaporated. The residue is taken up in ethyl acetate, washed with a sodium bicarbonate solution, dried over sodium sulfate, filtered, and evaporated. Crystallization from ethyl acetate/heptane gives 530 mg of the title compound, m.p. 171°–2° C., $[\alpha]_D^{25}$=−68.63° (c=1.02 in CH$_3$OH). UV, IR and $^1$H-NMR spectra correspond to those of the enantiomer described in Example 9, and the racemic compound of Example 6.

EXAMPLE 13

10-SYN-(+)-(2S,5S,10R)-7ACETYLOXY-2,3-DIHYDRO-10HYDROXY-2,6,8,9-TETRAMETHYL-2,5-METHANO-5-H-1,4-BENZODIOXEPIN-3ONE

An approximately 0.1 M solution of dimethyldioxirane in acetone is obtained by adding 250 g of potassium peroxymonosulfate (oxone$^R$) in portions to a stirred suspension of 120 g of sodium bicarbonate in 200 ml of water and 140 ml of acetone under a partial vacuum of about 150 mm and collecting the distillate in a dry ice-acetone-cooled trap. This solution (100–120 ml) is added to 3.04 g (1 mmol) of methyl 2S-(−)-6-acetyloxy-2,5,7,8-tetramethyl-2-H1-benzopyran-2-carboxylate (described in Example 2) in 50 ml of acetone and the mixture is stirred at room temperature for 2 hours. The solution is dried over magnesium sulfate, filtered, and evaporated to dryness at room temperature under reduced pressure to give 3.74 g of the crude epoxide, that is quite unstable, and to which is added immediately 1.96 g of anhydrous potassium acetate and 20 ml of acetic acid. The mixture is heated to reflux temperature for 1 hour, evaporated to dryness, and taken up in ethyl ether. The resulting solution is washed with water, a saturated sodium bicarbonate solution, and a saturated sodium chloride solution, filtered and evaporated to give 2.96 g of an oil. Chromatography on silica gel in ethyl acetate/hexane:½, gives several fractions, one of which (2.36 g) is recrystallized from ethyl acetate/hexane to give the title compound, m.p. 200°–201° C. $[\alpha]_D^{25}$=+78.04 (c=1.02 in CH$_3$OH). UV(CH$_3$CN)$\epsilon_{max}$ 289 nm ($\epsilon$=2037), 283 (sh), 224 (sh), 206 (42685); IR (KBr) 1798, 1734 cm$^{-1}$; $^1$H-NMR (DMSO), $\delta$ (ppm vs TMS) 6.30 (1, m, OH), 5.67 (1, d, J =6 Hz, 5-H), 4.44 (1, dd, J$_1$=4, J$_2$=6 Hz, 10-H), 2.43 (3, s, COCH$_3$), 2.07–2.17 (9, 3s, Ar—CH$_3$), 1.62 (3, s, 2—CH$_3$).

EXAMPLE 14

TRANS, TRANS-(−)-(2S,3R,4R)-3,4-DIHYDRO-3,4,6-TRIHYDROXY-2,5,7,8-TETRAMETHYL-2-H-1-BENZOPYRAN-2-CARBOXYLIC-ACID

To a solution of 460 mg (1.5 mm) of the lactone acetate described in the preceding example in 10 ml of methanol under nitrogen is added 10 ml of 2 N NaOH and the mixture is heated to reflux temperature for 30 minutes. The solution is cooled, acidified with 15 ml of 2 N HCl, and concentrated to remove methanol. The residue is saturated with sodium chloride and extracted twice with ethyl acetate. The extract is dried over sodium sulfate, filtered and evaporated. Crystallization of the residue from ethyl acetate/hexane gives 270 mg of the title compound $[\alpha]_D^{25}$=−41.88° (c=1.01 in H$_2$O, pH=3.20). UV (H$_2$O)$\lambda_{max}$ 292 nm ($\epsilon$=3441), 221 (11197); IR (KBr) 1741 cm$^{-1}$; $^1$H-NMR(DMSO), $\epsilon$ (ppm vs TMS) 4.48 (1, d, J=2.5 Hz, 4-H), 4.09 (1, d, J=2.5 Hz, 3-H).

EXAMPLE 15

10-SYN-(+)-(2S,5R,10S)-2,3DIHYDRO-7,10-DIHYDROXY-2,6,8,9-TETRAMETHYL-2,5-METHANO-5-H-1,4-BENZODIOXEPIN-3ONE

Treatment of 1.18 g of the acid described in the preceding example with ethereal hydrogen chloride, as described in Example 12, gives the title compound, m.p. 185° C., $[\alpha]$= +93.55° (c=1.07 in CH$_3$OH). UV (CH$_3$CN) $\lambda_{max}$ 298 nm ($\epsilon$=3567), 224 (sh), 206 (39200); IR(KBr) 1763 cm$^{-1}$; $^1$H-NMR(CD$_3$OD), $\epsilon$ (ppm vs TMS) 5.49 (1d, J=4.5, 5-H), 4.21 (1, d, J=4.5, 10-H); MS: MH$^+$=265.

EXAMPLE 16

10-SYN-(−)-(2R,5S,10R)-7-Acetyloxy-2,3DIHYDRO-10-HYDROXY-2,6,8,9-TETRAMETHYL-2,5-METHANO-5-H-1,4-BENZODIOXEPIN-3ONE Following the procedure described in Example 13, but starting from the 2R-(+)-enantiomer described in Example 3, the title compound is obtained, m.p. 203°–4° C., $[\alpha]_D^{25}$= −81.27 (c=0.95 in CH$_3$OH). UV, IR and $^1$H-NMR spectra correspond to those of the enantiomer described in Example 13.

EXAMPLE 17

METHYL CIS, TRANS-(2R,3R,4R)-4,6-DIACETYLOXY-3,4-DIHYDRO-3-DIHYDROXY-2,5,7,8-TETRAMETHYL2-H1-BENZOPYRAN-2-CARBOXYLATE

In the reaction described in the preceding example, a second product is obtained, which is assigned the structure of the title compound on the basis of the NMR spectrum. $^1$H-NMR (CDCl$_3$) $\delta$ (ppm vsTMS) 5.83 (1, d, J=2.9 Hz, 4-H), 4.29 (1, m, 3-H), 2.67 (3, s, OCH$_3$), 2.32 (3, s, COCH$_3$), 2.22 (3, s, COCH$_3$) 1.92–2.08 (9, 3s, ArCH$_3$), 1.70 (3, s, 2—CH$_3$); m.p. 180° C.

EXAMPLE 18

METHYL CIS, TRANS-(2R,3R,4R)-6-ACETYLOXY-3,4-DIHYDRO-3,4-DIHYDROXY-2,5,7,8-TETRAMETHYL-2-H1-BENZOPYRAN-2-CARBOXYLATE

An 0.1 M solution of dimethyldioxirane in acetone (60 ml), prepared as described in Example 13, is added to 1.37 g (4.5 mmol) of 2R-(+)-olefine (Example 3) in acetone. The mixture is stirred at room temperature for 1.5 hours to form the epoxide. Five drops of water and about 0.2 g of silica gel are added to the solution and stirring is continued overnight. The main product, as indicated by thin layer chromatography, is isolated by chromatography, 0.83 g, and is recrystallized from ethyl acetate/hexane. MS: $MNH_4^+$=356; $^1$H-NMR (CDCl$_3$) δ (ppm vs TMS) 4.70 (1, d, J= 2.9, 4-H), 4.18 (1, m, 3-H), 3.67 (3, s, OCH$_3$), 2.33 (3, s, COCH$_3$), 2.05–2.13 (9, 3s, Ar—CH$_3$), 1.70 (3, s, 2—CH$_3$).

EXAMPLE 19

TRANS, TRANS-(+)-(2R,3S,4 S)-3,4-DIHYDRO-3,4,6 -TRIHYDROXY-2,5,7,8-TETRAMETHYL-2- H-1-BENZOPYRAN-2-CARBOXYLIC ACID

The lactone acetate described in Example 16 is hydrolyzed with 1N 50% methanolic NaOH, as described in Example 14 to obtain the title compound, $[α]_D^{25}$=+34.6 (c =0.77 in CCl$_3$/CH$_3$OH: 2/1). UV, IR and $^1$H-NMR spectra correspond to those of the enantiomer described in Example 14.

EXAMPLE 20

10-SYN-(−)-(2R,5S,10 R)-2,3DIHYDRO-7,10-DIHYDROXY-2,6,8,9- TETRAMETHYL-2,5-METHANO-5- H-1,4-BENZODIOXEPIN-3-ONE

A solution of 1.22 g of the acid described in the preceding example in 70 ml of toluene containing 0.1 g of p-toluenesulfonic acid is refluxed for 1 hour. After cooling and addition of some ethyl acetate, the solution is washed with a sodium bicarbonate solution, dried over sodium sulfate, filtered and evaporated to give 0.77 g of oil. Crystallization from ethyl acetate/hexane gives the title compound, m.p. 178° C., $[α]_D^{25}$=−83.8° (c=0.933 in CH$_3$OH). UV, IR and $^1$H-NMR spectra correspond to those of the enantiomer described in Example 15.

EXAMPLE 21

11- SYN-(±)-8-ACETYLOXY-2,3,4,6-TETRAHYDRO- 11-HYDROXY-2,7,9,10-TETRAMETHYL-2,6- METHANO-1,5-BENZODIOXOCIN-4-ONE

Following the procedure described in Example 1, (2R, S)-3,4-dihydro-6-hydroxy-2,5,7,8-tetramethyl-2 H-1-benzopyran-2-acetic acid is esterified, acetylated, and dehydrogenated with DDQ to give methyl ((2R, S)-6-acetyloxy-2,5,7,-tetra-methyl-2 H-1-benzopyran-2-acetate, $^1$H-NMR (CDCl$_3$) δ (ppm vsTMS) 6.52 (1, d, J=10, 4-H), 5.72 (1, d, J=10, 3-H), 3.61 (3, s, OCH$_3$), 2.68 (2, s, COCH$_2$), 2.31 (3, s, COCH$_3$), 2.02–2.10 (9, 3s, ArCH$_3$), 1.56 (3, s, 2—CH$_3$).

Cis-hydroxylation with osmium tetroxide, as described in Example 4, gives two products that are separated by column chromatography on silica gel. One is the title compound, m.p. 179°–81° C. MS: $MNH_4^{30}$=338; IR (KBr) 1762, 1714 cm$^{-1}$ $^1$H-NMR (CDCl$_3$) δ (ppm vsTMS) 5.38 (1, d, J=3, 6-H), 4.07 (1, d, J=3, 11-H), 2.88 (1, d, J=20, COCH$_2$), 2.68 (1, d, J=20, COCH$_2$), 2.31 (3, s, COCH$_3$), 2.02–2.12 (9, 3s, Ar—CH$_3$), 1.61 (3, s, 2—CH$_3$).

EXAMPLE 22

TRANS, CIS-(±)-6-ACETYLOXY-3,4-DIHYDRO-3,4- DIHYDROXY-2,5,7,8-TETRAMETHYL-2- H-1-BENZOPYRAN-2-ACETIC ACID, METHYL ESTER

The second product obtained in the reaction described in the preceding example is the title compound, m.p. 135°–145° C., identified by its MS ($MNH_4^+$=370) and the hydrolysis product described in the next example.

EXAMPLE 23

TRANS, CIS-(±)-3,4DIHYDRO-3,4,6-TRIHYDROXY- 2,5,7,8-TETRA-METHYL-2-H-1 BENZOPYRAN-2-ACETIC ACID, METHYL ESTER

To a solution of 930 mg of the acetate, described in the preceding example, in 30 ml of methanol under nitrogen, is added a solution of 4.0 g of potassium carbonate in 20 ml of water and the mixture is stirred at room temperature overnight. After acidification with 2N HCl and evaporation of methanol, the product is extracted into ethyl acetate and the extract is washed with a sodium bicarbonate solution and dried over sodium sulfate, filtered, and evaporated. Recrystallization from ethyl acetate/heptane gives 440 mg of the title compound, m.p. 162°–3° C. IR (KBr) 1716 cm$^{-1}$; $^1$H-NMR (CDCl$_3$) δ (ppm vs× TMS) 7.26 (1, s, ArOH), 4.87 (1, d, J=5, 4-H), 4.08 (1, d, J=5, 3-H), 2.82 (2, s, CH$_2$CO), 2.31 (3, s, COCH$_3$), 2.10–2.31 (9, 3s, ArCH$_3$), 1.45 (3, s, 2—CH$_3$).

EXAMPLE 24

CIS, CIS-(±)-6ACETYLOXY-3,4-DIHYDRO-3,4 DIHYDROXY-2,5,7,8-TETRAMETHYL-2- H-1-BENZOPYRAN-2-CARBOXAMIDE

To a solution of 18.62 g of the olefin described in Example 1, in 200 ml of methanol under nitrogen is added 200 ml of 2N NaOH and the mixture is refluxed for 5 hours. After cooling, the mixture is acidified with 220 ml of 2 HCl and methanol is removed by evaporation. The product is extracted into ethyl acetate, and the extract is washed with a sodium bicarbonate solution. Acidification and reextraction with ethyl acetate gives (2R, S)-6-hydroxy2,5,7,8-tetramethyl-2- H-1-benzopyran-2-carboxylic acid. The acid is dissolved in 100 ml of acetic anhydride and heated to boiling, allowing the acetic acid that is formed to escape. Excess acetic anhydride is removed by evaporation under reduced pressure. The residue is dissolved in 300 ml of dry tetrahydrofuran and the solution is saturated with gaseous ammonia with cooling. After stirring at room temperature for 2 hours, the mixture is evaporated to dryness, the residue is taken up in ethyl acetate, washed with 2N HCl, water, and a NaHCO$_3$ solution, dried over Na$_2$SO$_4$, filtered and evaporated. The residue is recrystallized from ethyl acetate/heptane to give 8.15 g of (2R,S)-6-acetoxy-2,5,7,8-tetramethyl-2- H-1-benzopyran-2-carboxamide.

Cis-hydroxylation with osmium tetroxide, following the procedure described in Example 4, gives a crude product that is subjected to column chromatography on silica gel. One of the fractions is recrystallized from ethyl acetate/ heptane to give 1.1 g of the title compound. IR (KBr) 1758, 1702 cm$^{-1}$; $^1$H-NMR (DMSO)δ (ppm vs TMS) 4.68 (1, d, J=4, 4-H), 3.82 (1, d, J=4, 3-H) which indicates a cis,cis rather than a trans,cis configuration; MS: MNH$_4^+$=341.

The compounds of this invention are free radical scavengers. Free radical reactions have been implicated in the pathology of more than 50 human diseases. Radicals and other reactive oxygen species are formed constantly in the human body both by deliberate synthesis (e.g. by activated phagocytes) and by chemical side-reactions. They are removed by enzymic and non-enzymic antioxidant defence systems. Oxidative stress, occurring when antioxidant defences are inadequate, can damage lipids, proteins, carbohydrates and DNA. A few clinical conditions are caused by oxidative stress, but more often the stress results from the disease and can make a significant contribution to the disease pathology. For a more detailed review see B. Halliwell in *Drugs*, 1991, 42, 569–605.

There is a growing body of information that suggests a pathophysiologic role of oxygen free-radical-mediated lipid peroxidation following central nervous system trauma or stroke, either ischemic or hemorrhagic. A reduction in cerebral tissue concentration of endogenous antioxidants has been observed, as well as an increase in lipid peroxidation products. Inhibitors of brain lipid peroxidation counteract and reduce cerebral tissue damage, as well as to prolong life of traumatized animals. These findings have been reviewed by E. D. Hall and J. M. Braughler in *Free Radical Biology and Medicine*, 1989, 6, 303–313 and elsewhere. M. Miyamoto et al., (*J. Pharmacol. Exp. Ther.*, 1989, 250, 1132) report that neurotoxicity due to excessive glutamine release is similarly reduced by antioxidants. They suggest the use of agents that inhibit brain lipid peroxidation for treatment of neurodegenerative diseases such as Huntington's and Alzheimer's disease in which excessive glutamic acid release has been observed. M. R. Hori et al., (*Chem. Pharm. Bull.* 1991, 39, 367) report on anti-amnesic activity of brain lipid peroxidation inhibitors in rats. The role of oxygen free radicals in Parkinson's disease has been reviewed recently (*Free Radical Biol. Med.*, 1991, 10, 161–169) and a free radical scavenger has been tested clinically with some success (*Fundam. Clin. Pharmacol.*, 1988, 2, 1–12).

Ischemia followed by reperfusion causes formation of oxygen-derived free radicals and increased lipid peroxidation and results in tissue injury. Administration of free radical scavengers to animals subjected to ischemia/reperfusion reduces these effects in heart, lung, kidney, pancreas, brain and other tissues.

Vitamin E, i.e., α-tocopherol, a well known compound of the formula

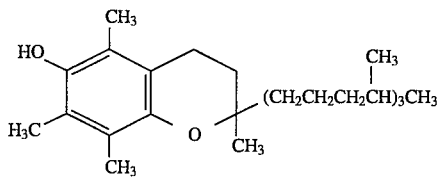

is a natural anti-oxidant that reacts with oxygen-derived free radicals as well as hydrogen peroxide. It has been shown that it is intercalated in lipid membranes and that its biological function is to protect biomembranes against oxidative attack. The antioxidant 3,4-dihydro-2,5,7,8-tetramethyl-2-H-2-benzopyran-6-ol moiety of α-tocopherol is constantly regenerated by the ubiquitous redox systems.

The compounds of the present invention are also useful in treating the process of inflammation which is known to involve the release of superoxide radicals from phagocytic cells which cause some of the symptoms of rheumatoid arthritis and other inflammatory diseases such as ulcerative colitis and inflammatory dermatological disorders such as psoriasis. Of particular use of this anti-inflammatory effect of the compounds of this invention is the treatment of inflammatory lower bowel disease.

Inhalation injury of the lungs is typically caused by heat and chemical irritation, and chemical injury is the leading lethal cause of smoke inhalation injury. Smoke inhalation leads to lung injury due to an increase in pulmonary microvasculature and pulmonary edema. This process is accompanied by increased lipid peroxidation in lung tissue. An inhibitor of lipid peroxidation was shown to reduce these symptoms in animals subjected to hot sawdust smoke by Z. Min et al., (*J. Med. Cell. PLA*, 1990, 5, 176–180). They suggest the use of antioxidants in treatment of smoke inhalation-lung injury, adult respiratory distress syndrome and emphysema.

Reactive oxygen species also play a role in the formation of foam cells in atherosclerotic plaques (reviewed by D. Steinberg et al., *New Engl. J. Med.*, 1989, 320, 915–924) and the free radical scavenger probucol has a marked antiatherosclerotic effect in hyperlipidemic rabbits (Carew et al., *Proc. Nat. Acad. Sci.* USA, 1987, 84, 7725–7729. Degenerative retinal damage and diabetogenic retinopathy have also been listed as target for treatment with free radical scavengers (cf. J. W. Baynes, *Diabetes*, 1991, 40, 405–412; S. P. Wolff et al., *Free Rad. Biol. Med.*, 1991, 10, 339–352).

The compounds may also be useful in the treatment of cancers, and degenerative diseases related to aging, stroke, and head trauma, since oxygen-derived free radicals have been identified among causative factors. For reviews, see B. Halliwell and C. Gutteridge, *Biochem. J.*, 1984, 219, 1–14; TINS 1985, 22–6. Antioxidants have also been shown to be useful in the treatment of cataracts, *Free Rad. Biol. Med.*, 12:251–261 (1992).

In vitro and in vivo activity for the compounds of this invention may be determined by the use of standard assays which demonstrate the free radical scavenging property, affinity for cardiac tissue and cardioprotective properties, as well as by comparison with agents known to be effective for these purposes.

Exemplary of the assay useful for determining the free-radical scavenging property of the compounds of this invention is by the in vitro inhibition of lipid peroxidation in rat brain homogenates.

The free radical scavenging properties of the compounds may readily be evaluated wherein superoxide radicals are generated by 4 mU of xanthine oxidase in the presence of 0.1 mM xanthine and detected by reduction of 40 μM nitro blue tetrazolium (NBT) to the diformazan dye in a spectrophotometric assay as described by C. Beauchamp and I. Fridovick, (*Analyt. Biochem.* 1971, 44, 276–287). 30 U of superoxide dismutase inhibited this reduction by 90% which is due to superoxide radicals. In the presence of a superoxide scavenger (test compound) there is a competition for the superoxide radical and thus a reduction in the color formation of NBT demonstrates the superoxide radical scavenging property of the test compound.

Inhibiting the process of lipid peroxidation may be assayed using tissue homogenates for measuring the antioxidant activity of biological fluids by the methodology of J. Stocks et al., (*Clin. Sci. Mol. Med.*, 1974, 47, 215–222), wherein a brain tissue homogenate of treated adult Sprague Dawley rats is utilized.

Samples of total volume 1 ml of diluted brain homogenate and with the scavenger at an appropriate dilution are incubated. Non-incubated samples are taken as background. Controls are run without scavenger and a sample containing only buffer is taken as blank. After incubation at 37° C. for 30 minutes, 200 µl of 35% perchloric acid is added, the samples centrifuged and 800 µl of the supernatants mixed with 200 µl of 1% thiobarbituric acid. The pink condensation product of thiobarbituric acid reactive material is developed at 100° C. in a boiling water bath for 15 minutes, and absorbance read at 532 nm.

For ex vivo inhibition of tissue including heart or brain tissue, lipid peroxidation in mice may be utilized to demonstrate the ability of the compounds to penetrate and act as free radical scavengers in these tissues. This assay involves pretreatment of male CD1 mice by subcutaneous administration of the test compound. One hour later the tissues are excised, homogenized 1+9 (w/v) in 20 mM potassium phosphate buffer at pH 7.3 (0.14 M KCl) and incubated at 1/100 concentration in 1 ml of buffer at 37° C. for 30–120 minutes. At the end of the incubation 200 µl of 35% perchloric acid is added and proteins removed by centrifugation. To 800 ml of the supernatant are added 200 µl of 1% TBA and the samples are treated to 100° C. for 15 minutes. The TBA-adduct is extracted into 2 times 1 ml of n-butanol. The fluorescence is measured at an excitation wavelength of 515 nm and an emission wavelength of 553 nm against a standard prepared from malondialdehyde dimethylacetal.

Stimulated human leukocytes release radicals and other oxygen metabolites, which, during inflammation, act as microbicidal agents. At the same time, they release proteolytic enzymes, such as elastase, which are also microbicidal but potentially threaten the connective tissue of the host. An endogenous $\alpha_1$-proteinase inhibitor ($\alpha_1$Pi) normally protects the host tissue from protelytic digestion. $\alpha_1$Pi is however, inactivated by the leukocyte-derived oxidants. Antagonism of the inactivation of $\alpha_1$Pi is an indication of the disclosed radical scavengers. The concentration needed to protect 50% of the elastase inhibitory capacity of $\alpha_1$Pi ($PC_{50}$) depends on the amount of stimulated leukocytes present.

Method: The procedure described by Skosey and Chow was followed (see J. L. Skosey and D. C. Chow in *Handbook of Methods for Oxygen Radical Research* (Greenwald, R. A., ed.) 1985, pp.413–416, CRC Press, Boca Raton). In short, human $\alpha_1$Pi was incubated with zymosan-stimulated human peripheral-blood leukocytes in the absence or presence of the scavengers. The amount of a $\alpha_1$Pi protected from oxidative inactivation was determined by its residual elastase inhibitory capacity.

Inhibition of 5lipoxygenase can be determined on purified enzyme obtained from rat basophilic leukemia (RBL-1) cells. The assay is described by J.-F. Navé et al., *Prostaglandins*, 1988, 36, 385–398 and in *Biochem. J.*, 1991, 278, 549–555. Eicosa-5(Z), 8(Z)-dienoic acid is used as substrate and the oxygenated products (5-hydroperoxy- and 5-hydroxyeicosa-6,8-dienoic acids) are extracted and analyzed by HPLC.

The relevance to inflammation matter has been reviewed by Weiss (see S. J. Weiss, *N. England J. Med.*, 1989, 320, 365–376). Lung emphysema is associated with a genetic defect in $\alpha_1$Pi; the disease is further enhanced by oxidants inhaled during cigarette smoking, which leads to oxidative inactivation of $\alpha_1$Pi in the lung tissue (see J. Travis and G. S. Salvesen, *Annu. Rev. Biochem.*, 1983, 52, 655–709). Oxidized $\alpha_1$Pi has also been isolated from rheumatoid synovial fluid (see P. S. Wong and J. Travis, *Biochem. Biophys. Roc. Commun.*, 1980, 06, 1440–1454). The degradation of hyaluronic acid, a macromolecule accounting for the viscosity of synovial fluid, is triggered by superoxyl radicals released from human leukocytes in vitro (see R. A. Greenwald and S. A. Moak, *Inflammation*, 1986, 10, 15–30). Furthermore, nonsteroidal anti-inflammatory drugs were shown to inhibit the release of superoxyl radicals from leukocytes (see H. Strom and I. Ahnfelt-Ronne, *Agents and Actions*, 1989, 26, 235–237 and M. Roch-Arveiller, V. Revelant, D. Pharm Huy, L. Maman, J. Fontagne, J. R. J. Sorenson and J. P. Giroud, *Agents and Actions*, 1990, 31, 65–71), and 5-aminosalicylic acid may exert its therapeutic activity in inflammatory bowel disease by a radical scavenger mechanism (see I. Ahnfelt-Ronne, O. H. Nielsen, A. Christensen, E. Langholz, V. Binder and P. Riis, *Gastroenterology*, 1990, 98, 1162–1169). Therefore, it is believed that the compounds of this invention may be useful in the mentioned pathologic situations and that inflammatory bowel disease may be a special target. An immune stimulatory effect of antioxidants has also been reported in that they enhanced lymphocyte activity (R. Anderson and P. T. Lukey, *Ann. N.Y. Acad. Sci.*, 1987, 498, 229–247) in vitro in the presence of triggered leukocytes, and ex vivo after pretreatment of human volunteers.

Thus, using standard and well known methodology, as well as by comparison with known compounds found useful, it is to be found that the compounds are free radical scavengers useful in the prevention and treatment of such disease states related to neurotoxicity due to excessive glutamic acid release, to Huntington's disease, Alzheimer's disease and other cognitive dysfunctions, (e.g. memory, learning and attention deficits), amnesia, and Parkinson's disease, as well as the treatment and prevention of tissue damage in heart, lung, kidney, pancreas and brain tissues induced by ischemia/reperfusion, and to allay acute blood loss due to hemorrhagic shock.

The compounds of this invention can be utilized both prophylactically and therapeutically. The amount of active ingredient for therapeutic administration can vary over a wide range and is dependent upon such factors as the species of patient to be treated, its age, health, sex, weight, nature and the severity of the condition being treated. The term "patient" refers to a warm-blooded animal such as, for example, rats, mice, dogs, cats, guinea pigs, primates and humans. Generally, a therapeutically effective amount of the active ingredient to be administered will range from about 0.1 mg/k g to 30 mg/kg of body weight per day. For prophylactic administration, corresponding lower doses can be utilized. Preferably, the compounds of the present invention will be administered to the patient in combination with a pharmaceutically acceptable carrier which is any substance which aids in the administration of the compound without substantially affecting its therapeutic properties.

Most preferably, the compounds are administered intravenously particularly under crisis situations wherein it is essential that the therapeutic agent be gotten to its site of action as quickly as possible, such as in those emergency conditions caused by coronary infarction, stroke and surgical interventions, conditions which can cause severe reperfusion damage.

The compounds of this invention also can be orally administered, preferably using more active ingredient per day than when parenterally administered, preferably taking divided doses 3 to 4 times per day. Preferably, enteral administration in post "crisis" situations, particularly after release from hospitalized conditions. The compounds can be used in standard dosage unit forms such as tablets, capsules, dragees, lozenges, elixirs, emulsions, suspensions, and in cases wherein topical application is preferred by suppository or sub-lingual administration. Tablets and capsules containing from 100 to 400 mg of active ingredient are preferred modes of enteral administration. Of course, in the treatment of inflammation the preferred method of administration is by depot injection directly to the situs of the inflammation area with follow-up enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polyethylene glycol solutions. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. In certain topical and parenteral preparations, various oils can be utilized as carriers or excipients. Illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethylcellulose. In addition to these excipients, buffers, preservatives and emulsifying agents may also be added. Typical enema preparation of the retention type enema utilize small volumes, generally much less than about 150 mL for an adult, typically volumes of only a few milliliters are preferred. Excipients and solvents for use in retention anemas should, of course, be selected so as to avoid colonic irritation and should also be selected so as to minimize absorption of the various agents.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compounds of the present invention may be incorporated into an aerosol preparation by means commonly known to those skilled in the art. The aerosol preparation may be prepared for use as a topical aerosol or may be prepared for inhalation. The aerosol preparation may be in the form of a solution or suspension and may contain other ingredients such as solvents, propellants and/or dispersing agents. Typical examples of aerosol preparations are shown in *Remington's Pharmaceutical Sciences*, 18th ed., Mack Publishing Company, Easton, Pa. pp. 1694–1712 (990) incorporated herein by reference.

Of course, as is true in most instances wherein certain classes of chemical compounds have been found to have beneficial therapeutic end-use applications, certain sub-generic groups and certain specific compounds are preferred. In this instance the preferred compounds of Formula IB and preferably wherein R is methyl, $R_1$ is methyl, and/or n is zero. When $R_2$ is C(O)$R_3$, $R_3$ is preferably $C_{1-9}$ alkyl, more preferably $C_{1-6}$ alkyl and most preferably methyl.

What is claimed is:

1. A compound of the formulae

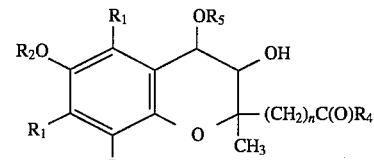

IA

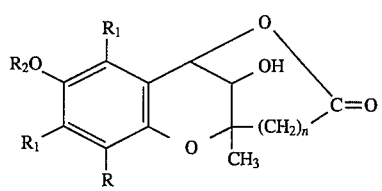

IB their individual stereoisomers and mixtures thereof, or the pharmaceutically acceptable salts thereof wherein R is H or $C_{1-4}$ alkyl, $R_1$ is $C_{1-4}$ alkyl, $R_2$ is H or $C(O)R_3$, $R_3$ is H or $C_{1-9}$ alkyl, $R_4$ is OR or $N(R)_2$, $R_5$ is H, —C(O)R or $C_{1-4}$ alkyl, and n is zero or one.

2. The compounds of claim 1 wherein the compound comprises Formula IB.

3. The compounds of claim 1 wherein the compound comprises Formula IA.

4. The compound of claim 1 wherein R is methyl.

5. The compound of claim 1 wherein $R_1$ is methyl.

6. The compound of claim 1 wherein n is zero.

7. The compound of claim 1 wherein $R_2$ is H.

8. The compound of claim 1 wherein $R_2$ is $C(O)R_3$ and $R_3$ is methyl.

9. A pharmaceutical composition comprising a compound of claim 1 and a pharmaceutically acceptable carrier.

10. The compound of claim 1 which is 10-anti-(±)-7-acetyloxy-2,3-dihydro-10-hydroxy-2,6,8,9-tetramethyl-2,5-methano-5-5H1,4-benzodioxepin-3-one.

11. The compound of claim 1 which is methyl trans, cis-(±)-6-acetyloxy-3,4-dihydro-3,4-dihydroxy-2,5,7,8 -tetramethyl-2-H-1-benzopyran-2-carboxylate.

12. The compound of claim 1 which is 10-anti-(±)-2,3-Dihydro-7,10-dihydroxy-2,6,8,9-tetramethyl-2,5-methano-5-H-1,4 -benzodioxepin-3-one.

13. The compound of claim 1 which is trans, cis-(±)-3,4-dihydro-3,4,6-trihydroxy-2,5,7,8-tetramethyl-2 H- 1-benzopyran-2-carboxylic acid.

14. The compound of claim 1 which is 10-anti-(+)(2S,5 R,10 R)-7-acetyloxy-2,3-dihydro-10-hydroxy-2,6,8,9-tetramethyl-2,5-methano-5-H-1,4-benzodioxepin-3-one.

15. The compound of claim 1 which is 10-anti-(+)(2S,5 R,10R)-2,3-dihydro-7,10-dihydroxy-2,6,8,9-tetramethyl-2,5-methano-5-H-1,4-benzodioxepin-3-one.

16. The compound of claim 1 which is 10-anti, -(-)(2 R,5S,10 S)-7-acetyloxy-2,3-dihydro-10-hydroxy-2,6,8,9-tetramethyl-2,5-methano-5-H1,4-benzodioxepin-3-one.

17. The compound of claim 1 which is cis, cis-(+)-(2 R,3S,4 S)-3,4-dihydro-3,4,6-trihydroxy-2,5,7,8-tetramethyl-2 H-1-benzopyran-2-carboxylic acid.

18. The compound of claim 1 which is 10-anti-(-)-(2 R,5S,10S)-2,3-dihydro-7,10-dihydroxy-2,6,8,9-tetramethyl-2,5-methano-5-H1,4-benzodioxepin-3-one.

19. The compound of claim 1 which is 10-syn-(+)-(2 S,5R,10 S)-7-acetyloxy-2,3-dihydro-10-hydroxy-2,6,8,9-tetramethyl-2,5-methano-5-H1,4-benzodioxepin-3-one.

20. The compound of claim 1 which is trans, trans-(-)-(2S,3R,4 R)-3,4-dihydro-3,4,6-trihydroxy-2,5,7,8-tetramethyl-2-H-1-benzopyran-2-carboxylic-acid.

21. The compound of claim 1 which is 10-syn-(+)-(2 S,5R,10S)-2,3-dihydro-7,10-dihydroxy-2,6,8,9-tetramethyl-2,5-methano-5-H-1,4-benzodioxepin-3-one.

22. The compound of claim 1 which is 10-syn-(-)-(2 R,5S,10R)-7-acetyloxy-2,3-dihydro-10-hydroxy- 2,6,8,9-tetramethyl-2,5-methano-5-H-1,4-benzodioxepin-3-one.

23. The compound of claim 1 which is methyl cis, trans-(2R,3R,4R)-4,6-diacetyloxy-3,4-dihydro-3-hydroxy-2,5,7,8-tetramethyl-2H1-benzopyran-2-carboxylate.

24. The compound of claim 1 which is methyl cis, trans-(2R,3R,4 R)-6-acetyloxy-3,4-dihydro-3,4-dihydroxy-2,5,7,8-tetramethyl-2 H-1-benzopyran-2-carboxylate.

25. The compound of claim 1 which is trans, trans-(+)-(2R,3S,4 S)-3,4-dihydro-3,4,6-trihydroxy-2,5,7,8-tetramethyl-2 H-1-benzopyran-2-carboxylic acid.

26. The compound of claim 1 which is 10-syn, -(-)-(2 R,5S,10 R)-2,3-dihydro-7,10-dihydroxy-2,6,8,9-tetramethyl- 2,5-methano-5-H-1,4-benzodioxepin-3-one.

27. The compound of claim 1 which is 11 syn-(±)-8-Acetyloxy- 2,3,4,6-tetrahydro-11-hydroxy-2,7,9,10-tetramethyl-2,6-methano-1,5-benzodioxocin-4-one.

28. The compound of claim 1 which is trans, cis-(±)-6-acetyloxy- 3,4-dihydro-2,5,7,8-tetramethyl-2-H-1-benzopyran-2-acetic acid, methyl ester.

29. A method of treating a patient for inflammatory bowel disease by administering to the patient an effective amount of a compound according to claim 1.

30. A method of treating a patient for reperfusion damage by administering to the patient an effective amount of a compound according to claim 1.

31. The process of making a compound of the formulae

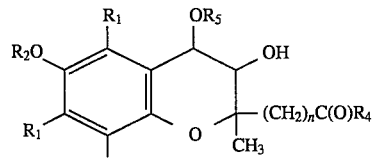

IA or

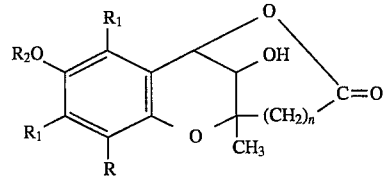

IB their individual stereoisomers and mixtures thereof, or the pharmaceutically acceptable salts thereof wherein R is H or $C_{1-4}$ alkyl, $R_1$ is $C_{1-4}$ alkyl, $R_2$ is H or $C(O)R_3$, $R_3$ is H or $C_{1-9}$ alkyl, $R_4$ is OR or $N(R)_2$, $R_5$ is H, —C(O)R or $C_{1-4}$ alkyl, and n is zero or one.

by dihydroxylation of the following compound

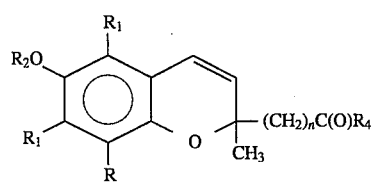

with an appropriate hydroxylating agent to give either the cis or trans compound having the formula 21
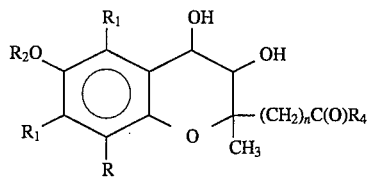
or when the 4-hydroxy group is cis to the acid function, that is when $R_4$ represents OH, to produce the lactone having the formula
22
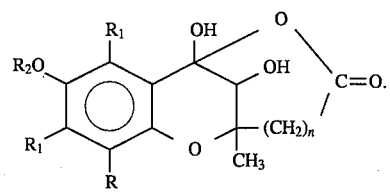
* * * * *